(12) United States Patent
Kawamura et al.

(10) Patent No.: US 6,297,057 B1
(45) Date of Patent: Oct. 2, 2001

(54) METHOD OF MEASURING CONCENTRATION OF SPECIFIC CONSTITUENT

(75) Inventors: Tatsurou Kawamura, Kyotanabe; Hiroshi Onishi, Hirakata; Nobuo Sonoda, Settsu, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/302,302

(22) Filed: Apr. 30, 1999

Related U.S. Application Data

(62) Division of application No. 08/964,756, filed on Nov. 5, 1997, now Pat. No. 6,036,922.

(30) Foreign Application Priority Data

Nov. 7, 1996 (JP) ................................................. 8-295283

(51) Int. Cl.$^7$ ................................................. G01N 33/493
(52) U.S. Cl. ................................ 436/86; 436/95; 436/164
(58) Field of Search .............................. 436/86, 87, 88, 436/93, 94, 95, 164

(56) References Cited

U.S. PATENT DOCUMENTS

| | | | |
|---|---|---|---|
| 3,713,738 | 1/1973 | Bernhardt | 356/365 |
| 4,309,110 | 1/1982 | Tumerman | 356/365 |
| 4,801,552 | 1/1989 | Hoff | 436/173 |
| 5,096,833 | 3/1992 | Lau et al. . | |
| 5,124,266 | 6/1992 | Coryn et al. . | |
| 5,162,236 | 11/1992 | Pang et al. | 436/73 |
| 5,168,326 | 12/1992 | Tokieda et al. | 356/368 |
| 5,212,099 | 5/1993 | Marcus | 436/172 |
| 5,241,363 | 8/1993 | Garner | 356/326 |
| 5,492,834 | 2/1996 | Liu et al. . | |
| 5,593,895 | 1/1997 | Cahill et al. . | |

FOREIGN PATENT DOCUMENTS

| | | |
|---|---|---|
| 0 805 352 | 5/1997 | (EP) . |
| 94/18228 | 8/1994 | (WO) . |
| 97/18470 | 11/1996 | (WO) . |

OTHER PUBLICATIONS

Koksharova, T.E. et al, Derwent Acc No. 1986–034413, abstract for Patent Publication SU 1167501, Jul. 15, 1985.*
Druzhinin, A.A. et al, Derwent Acc No. 1979–67619B, abstract for Patent Publication SU 636534, Dec. 10, 1978.*
Shulga, A.V. et al, Derwent Acc No. 1988–290853, abstract for Patent Publication SU 1383201, Mar. 23, 1988.*
Kitabatake, N. et al, Chemical Abstract No. 123:142091, Turbidity Measurement of Heated Egg Proteins Using a Microplate System, Food Chemistry, vol. 54, 1995, pp. 201–203.*

* cited by examiner

Primary Examiner—Jeffrey Snay
(74) Attorney, Agent, or Firm—McDermott, Will & Emery

(57) ABSTRACT

The present invention provides a measuring method most suitable for measuring the concentrations of specific constituents, especially urine protein level and sugar level. After a protein-contained liquid sample is opacified by heating or while the sample is being heated, a light is projected to the liquid sample. The concentration of protein is determined from the intensity of light transmitted through the sample or scattered from the sample. In a urinalysis, an angle of rotation of the sample is measured before the sample is opacified, and in addition, intensity of the transmitted light or scattered light of the opacified urine is measured, whereby the urine sugar and protein levels are obtained.

13 Claims, 14 Drawing Sheets

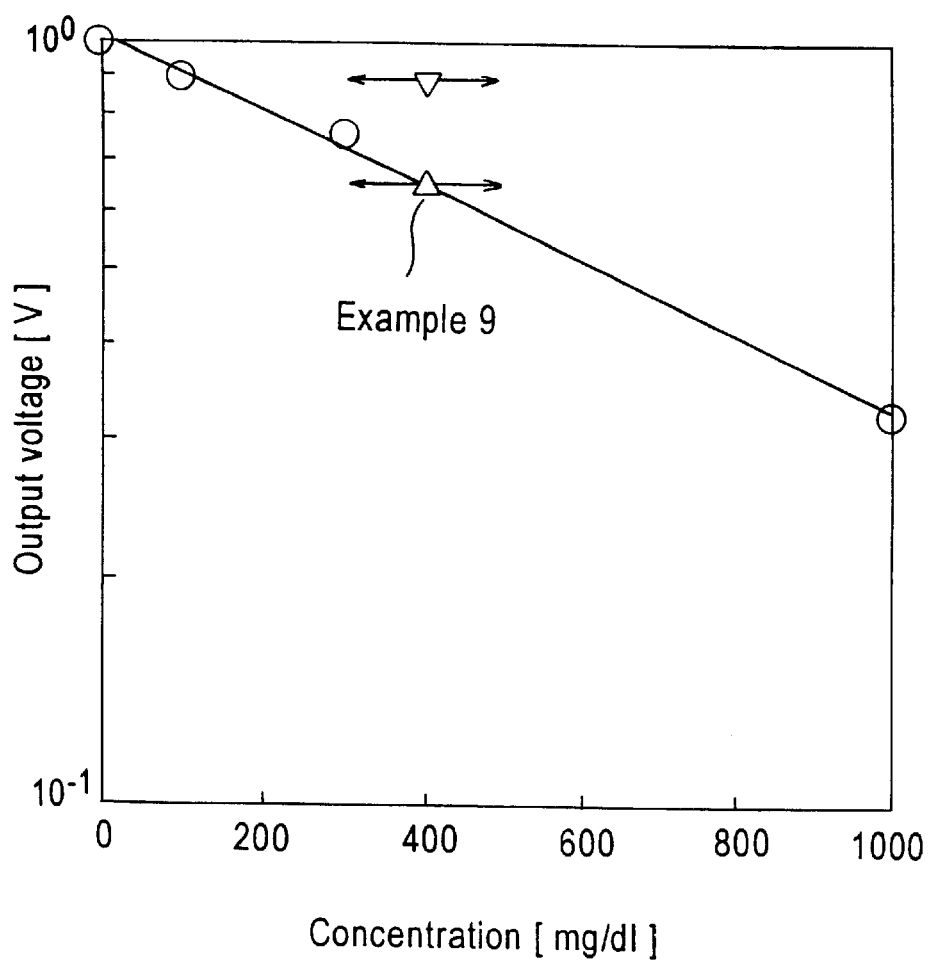

METHOD OF MEASURING CONCENTRATION OF SPECIFIC CONSTITUENT

This is a divisional application of Ser. No. 08/964,756 as originally filed on Nov. 5, 1997 now U.S. Pat. No. 6,036,922.

BACKGROUND OF THE INVENTION

The present invention relates to a method of measuring a concentration of a specific constituent in a liquid sample, more particularly a method of measuring a protein level (albumin concentration) and a sugar level (glucose concentration) of urine collected from humans or animals, and an apparatus for measuring them. The urine sugar level and urine protein level reflect the health conditions. So, an easy-to-use and accurate measuring method has been sought.

Hitherto, a urine test has been conducted by dipping a test paper impregnated with a reagent by a testing constituent such as sugar and protein into urine, and examining a color reaction of the test paper by a spectrophotometer. This test method requires different kinds of test papers for different testing constituents, and a new test paper is required for each test, thereby leading to a high running cost. There also has a limit to automatizing the process for labor saving.

When the urine test is done by this method at home, a layman should mount and replace test papers. It is not so pleasant a job and has been a block to the spread of the urine testing unit among the households.

Then, a urine test requiring no such expendable supplies as a test paper is proposed in an international patent application with a given international publication No. WO97/18470. The idea of this application is that the urine sugar and urine protein levels are quantified by measuring the angle of rotation of the urine since glucose and albumin are optically active, while other urine constituents show little optical rotatory power.

When a light is propagated through a liquid containing an optically active substance, the direction of polarization rotates in proportion to the concentration of the optically active substance. It is expressed in the following equation.

$$A = L \times \alpha \qquad (1)$$

where:

L: measuring optical path length

A: angle of rotation [degree]

α: specific angle of rotation of optically rotatory substance

If, for example, a light with a wavelength of 589 nm is propagated 100 mm through a glucose aqueous solution of 100 mg/dl in concentration, the direction of polarization of the light rotates $50 \times 10^{-3}$ degrees.

Utilizing such property, the sugar and protein levels in urine are calculated by using the above equation. Shown in Table 1 are the specific angles of rotations of aqueous solutions of glucose and albumin at 20° C.

TABLE 1

| Wavelength | 589 nm | 670 nm |
|---|---|---|
| Glucose | 50 degrees | 40 degrees |
| Albumin | −60 degrees | −43 degrees |

In a case N kinds of optically active substances are contained in a solution, the angle of rotation of the solution is given as follows:

$$A = L \times (\alpha_1 \times C_1 + \alpha_2 \times C_2 + \ldots + \alpha_N \times C_N) \qquad (2)$$

where:

L: measuring optical path length

A: angle of rotation [degrees]

$\alpha_{r1}$ (n=1, 2, ..., N): specific angle of rotation of substance n (N: natural number)

$C_{r1}$: concentration of substance n [kg/l]

$a_{r1}$: specific angle of rotation of substance n

As is evident from equation (2), the measured angle of rotation of the solution has an information about the concentrations of the plural optically active substances dissolved in the solution. That is, the angles of rotation measured of urine is a sum of the angle of rotation caused by glucose and that caused by albumin. Since the specific angle of rotation differs with the wavelength of propagated light, the angles of rotation are measured with different wavelengths of light in this method. And the sugar and protein levels in urine are calculated by simultaneous equations of equation (2).

In this method, with one wavelength of a light source, either the sugar or protein level in urine can be calculated if the concentration of the other is known. But if neither the sugar or protein level in urine is known, two or more light sources are required. Another shortcoming is that because there is not much difference between the change in specific angle of rotation of glucose which occurs with the change in light wavelength and that of albumin as shown in Table 1, no accurate determination of the sugar and protein levels in urine can be hoped for even if a plurality of light sources are used. Especially because the protein level in urine is smaller in one order of the magnitude than the sugar level, the accuracy in determination is low.

BRIEF SUMMARY OF THE INVENTION

It is accordingly an object of the present invention to provide a method of determining a concentration of a specific constituent in a liquid sample, especially a protein concentration with high accuracy, which is suitable for urinalysis, eliminating the problems mentioned above.

According to the present invention, a liquid sample containing protein is opacified by heating, and a light is then projected on the sample and the intensity of the light which passed through or scattered in the sample is measured. In this way, the concentration of protein in the sample can be determined accurately. This method is most suitable for urine test.

The healthy adult usually discharges 1,000 to 1,500 ml of urine a day. Of that amount, the total solid contents come to 50 to 70 g. Of the solid contents, about 25 g are inorganic substances which consist mainly of sodium chloride, potassium chloride and phosphoric acid. Most of them are dissolved and ionized in urine. The rest are organic substances, mainly urea and uric acid, but sugar or glucose and protein are also present through small in quantity. The protein in urine is essentially albumin. Glucose is discharged into urine usually in 0.13 to 0.5 g a day. From this and the amount of urine, the glucose level in urine or the urine sugar level is estimated at not larger than 50 mg/dl on the average. However, with diabetics, the figure is several hundred mg/dl and can be as high as several thousand mg/dl. In other words, the values for diabetics can be 10 to 100 times as high as the normal level. On the other hand, albumin is usually still less than glucose and discharged into the urine in 3 to 60 mg a day. Calculated from that and the amount of urine, the albumin concentration in urine or the urine protein level is estimated normally at not larger than 6 mg/dl. But the urine protein level in patients with kidney disorder can reach 100 mg or more/dl −10 times as high as the normal level.

Such abnormal protein levels in urine can be detected on the basis of the intensity of the transmitted or scattered light. Furthermore, measurement of the angle of rotation of urine provides information on optically active substances, that is, glucose and albumin. If, therefore, the angle of rotation of urine is determined in advance and the urine is then heated thereby being opacified, the urine sugar level can be determined with high accuracy by measuring the degree of the white turbidity. Urine samples which are difficult to be opacified by heating are mixed with a bivalent metal ion or acid before heating so as to facilitate whitening.

Thus realized is a urine test method ease to maintain and control, requiring no expendable supplies.

In the present invention, the intensity of the transmitted or scattered light is measured on a heat treated protein containing liquid sample. Determination can be made in another way in which a light is projected on the liquid sample being heated, and the intensity of the transmitted or scattered light is measured thereby determining the protein concentration from the change with the temperature of the liquid sample in those light intensities.

In still another method according to the present invention, while the sample is heated, the intensity of the transmitted or scattered light is measured at two different temperatures. The protein concentration can be calculated on the basis of intensity ratio in the two measurements of the transmitted or scattered light.

While the novel features of the invention are set forth particularly in the appended claims, the invention, both as to organization and content, will be better understood and appreciated, along with other objects and features thereof, from the following detailed description taken in conjunction with the drawings.

BRIEF DESCRIPTION OF THE SEVERAL VIEWS OF THE DRAWING

FIG. 16 is a characteristic diagram showing the relation between the concentration of albumin in urine mixed with acetic acid and the output voltage of the photosensor known from a still further embodiment of the present invention.

DETAILED DESCRIPTION OF THE INVENTION

Figure 1:
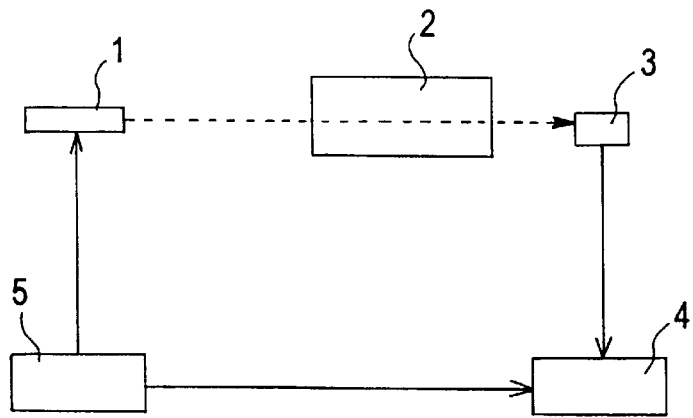
FIG. 1 is a schematic diagram showing the configuration of a measurement apparatus in an embodiment of the present invention.

The method of measuring the concentration of specific constituent according to the present invention comprises the steps of: heating a liquid sample containing protein to obtain an opacified sample; projecting a light on the opacified sample; detecting the light transmitted through the opacified sample or scattered from the opacified sample out of the projected light; and determining a concentration of protein in the liquid sample on the basis of the intensity of the detected light.

The measuring method according to the present invention is especially useful for urinalysis.

Urine is opacified and whitened when heated up to 60 to 80° C. That is because albumin, a protein contained in urine, coagulates into a macro colloid. The other constituents than albumin are all so small in molecular weight that the scattering of light on them can be ignored. It is also noted that heating up to that temperature will not affect the other constituents including glucose. On this ground, the intensity of the light transmitted through urine or scattered from urine out of the light projected on the urine depends on the urine protein level. Within the albumin concentration range where the urine protein level is measurable, it is considered that the intensity of the transmitted light is roughly proportional to the urine protein level. That is to say, it is possible to determine the albumin concentration in urine or urine protein level by projecting a light on opacified urine, measuring the intensity of the scattered or transmitted light and comparing it against a prepared analytical line (a relational expression between the albumin concentration of the aqueous solution and the scattered or transmitted light intensity).

In urinalysis, substantially parallel light rays with a wavelength of not shorter than 500 nm are projected on a urine sample. The specific angle of rotation of an optically active substance increases with the decrease of wavelength as shown in Table 1 until abnormal scattering by optically rotatory dispersion appears. This means that the shorter the wavelength of light rays, the higher the determination accuracy. With light rays with a wavelength of not longer than 500 nm, however, the absorbance by urine constituents like urochrome increases, making the determination less accurate on the contrary.

By measuring an angle of rotation of urine before heating, it becomes possible to determine a urine sugar level with high accuracy as well as the urine protein level. First, an intensity of the transmitted light or scattered light is checked against analytical line thereby calculating the urine protein level. Substituting the urine protein level and rotation angle obtained into equation (2) gives the urine sugar level.

In a preferred mode of the present invention, a light is projected on the protein-containing sample being heated, and measurement is taken of the intensity of the light transmitted through the sample or scattered from the sample out of the light projected on the sample. The white turbidity of the sample increases with the rise of temperature. So, if the sample is heated and the transmitted light or scattered light is detected simultaneously, the concentration of protein in the sample can be determined from those changes with temperature. It is not necessary to measure the intensity of the transmitted light or scattered light continuously. Instead, a determination can be made by measuring the intensity of the transmitted light or scattered light at only two points between 60 and 80° C., and using the ratio of these intensities. For example, the concentration of protein can be calculated from the ratio of the intensities of transmitted light at 75° C. to that at 70° C. According to this method, the influence of the transmittance of the sample before heating can be eliminated. That also can remove the influence of scattering and the like by substances other than protein.

Liquid samples containing proteins like urine are opacified when heated to 60 to 80° C. However, some samples with some compositions do not opacified by heating even containing an enough amount of protein. It is difficult to opacify urine with an unusually high pH value, for example. By adding bivalent metal ions like calcium ions and magnesium ions to such sample, it is possible to facilitate the coagulation of protein contained therein. They are added in the form of chloride, for example. In the case calcium ions are used, the amount of calcium ions to add is preferably not lower than 0.2 m mol (millimole) per 1 dl of the sample. In the case of magnesium ion, the amount of magnesium ions to add is preferably not lower than 0.1 m mol per 1 dl of the sample. In place of such bivalent metal ions, an acid can be added to the sample to lower the pH of the sample, preferably to 5.5 or below. This way, the coagulation of protein can similarly be promoted. The acid to add is preferably acetic acid or phosphoric acid.

The apparatus for measuring a concentration of a specific constituent of the present invention comprises: a sample cell to hold a liquid sample containing protein; a heater for heating the liquid sample in the sample cell; a temperature measurement unit for measuring the temperature of the liquid sample; a light source for projecting substantially parallel monochromatic light lays on the liquid sample; and a photosensor for detecting the light transmitted through the liquid sample out of the projected light and outputting a signal corresponding to the intensity of the light detected.

In a preferred mode of the present invention, the apparatus for measuring a concentration of a specific constituent further comprises a modulator for modulating the substantially parallel light rays projected from the light source and a lock-in amplifier for the phase-sensitive detection of a signal outputted from the photosensor referring to the signal modulated by the light modulation unit.

In another preferred mode of the present invention, the apparatus for measuring a concentration of a specific constituent comprises: a magnetic field application unit for applying a magnetic field on the liquid sample; a magnetic field sweep unit for sweeping the magnetic field; a magnetic field sweep unit for vibration-modulation of the magnetic field; a polarizer, mounted between the monochromatic light source and the sample cell, for transmitting a specific polarized light component only out of the substantially parallel light rays projected from the light source; an analyzer, provided before the photosensor, for transmitting a specific polarized light component only out of the substantially parallel light rays passed through the sample cell; a lock-in amplifier for the phase-sensitive detection of output signals from the photosensor referring to the signal modulated by the magnetic field modulation unit; and a calculator for calculating the angle of rotation of the liquid sample and intensity of the transmitted light on the basis of the output signal from the lock-in amplifier.

In still another preferred mode of the invention, the apparatus for measuring the concentration of specific constituent further comprises: a magnetic field application unit for applying a magnetic field on the liquid sample; a magnetic field sweep unit for sweeping the magnetic field; a magnetic field modulation unit for vibration-modulation of the magnetic field, a polarizer, mounted between the light source and the sample cell, for transmitting a specific polarized light component only out of the light rays projected from the light source; an analyzer for transmitting a specific polarized light component only out of the light rays passed through the sample cell; a photosensor for detecting the light transmitted through the analyzer and outputting a signal corresponding to the intensity of the detected light; a beam sampler to take out part of the light rays transmitted through the sample cell; a photodetection unit for detection of the light taken out by the beam sampler and for outputting a signal corresponding to the intensity of the detected light; a lock-in amplifier for the phase-sensitive defection of output signals from the photosensor referring to the signal modulated by the magnetic field modulation unit and receiving the output signal from the photodetection area at the same time; and a calculator for calculating the angle of rotation of the liquid sample and intensity of the transmitted light according to the output signal from the lock-in amplifier.

Another apparatus for measuring a concentration of a specific constituent of the present invention comprises: a sample cell to hold a liquid sample containing protein; a heater for heating the liquid sample in the sample cell; a temperature measurement unit for measuring the temperature of the test sample; a light source for projecting substantially parallel monochromatic light rays on the liquid sample; and a photosensor for detecting the light scattered from the liquid sample out of the projected light rays and outputting signals corresponding to the intensity of the light detected.

In a preferred mode of the present invention, the apparatus for measuring a concentration of a specific constituents comprises: a modulation unit for modulating the substantially parallel light rays; a magnetic field application unit for applying a magnetic field on the test sample; a unit for sweeping the magnetic field; a magnetic field modulation unit for vibration-modulation of the magnetic field; a polarizer, mounted between the light source and the sample cell, for transmitting a specific polarized light component only out of the light rays projected from the light source; an analyzer for transmitting a specific polarized light component only out of the light rays transmitted through the sample cell; a photosensor for detecting the light transmitted through the analyzer and for outputting signals corresponding to the intensity of the light detected; a photodetection unit for outputting signals corresponding to the intensity of the light detected; a lock-in amplifier for reception of signals from the photodetection unit and for the phase-sensitive defection of output signals from the photosensor referring to the signal modulated by the magnetic field modulation unit; and a calculator for calculating an angle of rotation of the liquid sample and the intensity of the transmitted light according to the output signal from the lock-in amplifier.

The present invention can utilized in determination of protein concentration in a solution. In addition, according to the present invention, it is also possible to determine concentrations of optically rotary substances further being contained in the solution. Hereafter, methods of determining the sugar and protein levels in urine are described in detail with reference to the accompanying drawings in embodiments of the present invention.

EXAMPLE 1

FIG. 1 shows a configuration of a measurement apparatus used in the present embodiment. An irradiation module 1 has an optical system with the semiconductor laser as a light source and a semiconductor laser driving circuit. This irradiation module 1 projects a substantially parallel light with a wavelength of 670 nm and an intensity of 5 mW on a sample cell 2. The sample cell 2 is cylindrical with the two ends 10 mm in diameter made of glass as transmitting surfaces and has a substantial light path length of 50 mm. A photosensor 3 detects the light projected from the irradiation module 1 and transmitted through the sample cell 2. A lock-in amplifier 4 makes phase-sensitive detection of the output signal of the photosensor 3 referring to a modulated signal emitted to the irradiation module 1 from a signal generator 5 and outputs a signal corresponding to the intensity of the transmitted light. Here, the signal generator 5 supplies a modulation signal to the irradiation module 1 so as to pulse-modulate the light to be projected from the irradiation module 1 in synchronization with that signal.

The light transmitted through a heat-treated urine sample was determined using this apparatus. This determination was performed in the following way. First, albumin solutions with a concentration of 100, 300 or 1,000 mg/dl were prepared with urine as a solvent of which the albumin concentration had been found to be not higher than 10 mg/dl by using a test paper. These albumin solutions and the urine used as the solvent were heated for 5 minutes at 75° C. and cooled down to 35° C. They were then poured into the respective sample cells 2 and the intensity of the transmitted lights were measured.

Figure 2:
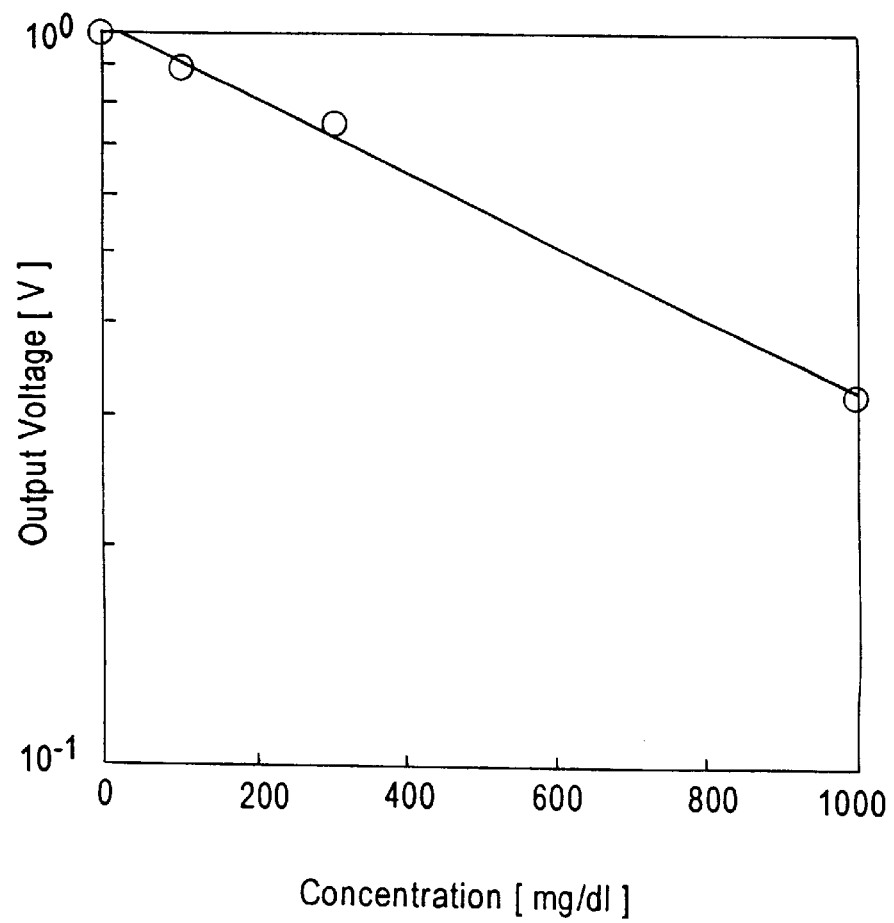
FIG. 2 is a characteristic diagram illustrating the output voltage in relation to the albumin concentration of the aqueous solution in measurements using the measurement apparatus.

The results or the output signals (voltage) from the lock-in amplifier 4 are plotted in FIG. 2. There, the output voltage is indicated logarithmically on the axis of ordinates and the concentration of the albumin solution on the axis of abscissas. The concentration of 0 represents the urine. As indicated, a relation between the output voltage and the albumin concentration is approximated to a straight line. By using this straight line as an analytical line, therefore, it is possible to determine the concentration of albumin or protein level in an unknown urine sample.

Using this apparatus, a urine sample was analyzed which had been found to have an albumin concentration of not lower than 100 mg/dl and not higher than 250 mg/dl by using a test paper. It showed that the output voltage of the lock-in amplifier 4 was 0.87 V. The concentration of albumin as found from the analytical line in FIG. 2 was 120 mg/dl, agreeing with the results obtained by using a test paper.

Similarly, another urine sample was analyzed which had been found to have an albumin concentration of not lower than 300 mg/dl and not higher than 500 mg/dl by using the test paper. The result was that the output voltage of the lock-in amplifier 4 was 0.63 V. The albumin concentration found from the analytical line shown in FIG. 2 was 400 mg/dl. It is in agreement with the results obtained by using the test paper.

As shown in the present embodiment, protein level of urine can be determined with high accuracy by heating the urine and measuring the intensity of the transmitted light after heating the urine. Besides, no expendable supplies like test papers are required. Therefore, this method is high in practicality.

EXAMPLE 2

Figure 3:
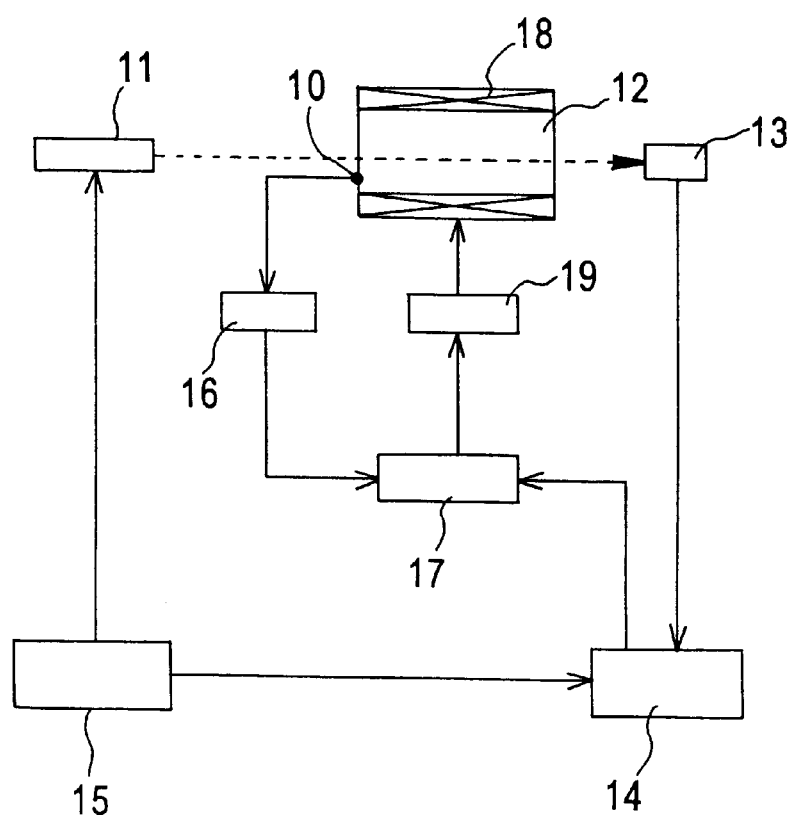
FIG. 3 is a schematic diagram showing the configuration of a measurement apparatus in another embodiment of the present invention.

The configuration of the measurement apparatus used in the present embodiment is shown in FIG. 3. In this embodiment, while heating a protein-containing liquid sample such as urine and detecting a temperature thereof, an intensity of a light transmitted through the liquid sample is measured. As in Example 1, a light is projected to a sample cell 12 from an irradiation module 11. The sample is poured into the sample cell 12. A photosensor 13 detects the light projected from the irradiation module 11 and transmitted through the sample cell 12. Then, a signal generator 15 supplies a modulation signal to the irradiation module 11 thereby pulse-modulating the light to be projected in synchronization with this signal. A lock-in amplifier 14 makes phase-sensitive detection of the output signal of a photosensor 13 referring to the modulation signal emitted to the irradiation module 11 from the signal generator 15. This output voltage of the lock-in amplifier 14 corresponds to the intensity of the transmitted light. Around the sample cell 12 is provided a solenoid coil-shaped heater 18 to heat the liquid sample in the sample cell 12. The heater 18 is formed with 500 turns of an enameled wire. A coiled heater driver 19 supplies the heater 18 with a current of up to 5 A according to the command from a computer 17. A thermocouple 10, mounted close to the sample cell 12, practically detects the temperature of the liquid sample in the sample cell 12. A temperature indicator 16 indicates the temperature of the liquid sample detected by the thermocouple 10 and sends the value to the computer 17. The output or intensity of the transmitted light detected by the lock-in amplifier 14 is also supplied to the computer 17. Then, the computer 17 send the heater driver 19 the command to heat the liquid sample according to the preset program. The computer 17 also measures the temperature of the liquid sample and the intensity of the transmitted light.

Figure 4:
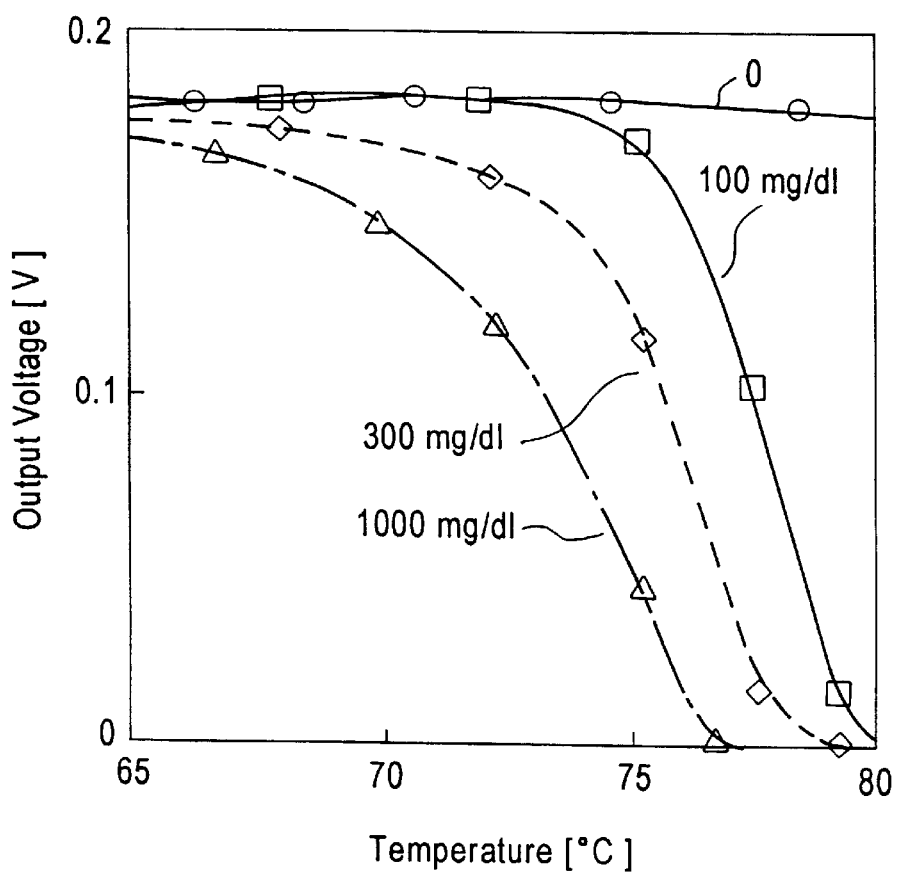
FIG. 4 is a characteristic diagram showing the relation of the temperature and output voltage of the photosensor to the albumin concentration of the aqueous albumin solution in measurements using the measurement apparatus
Figure 5:
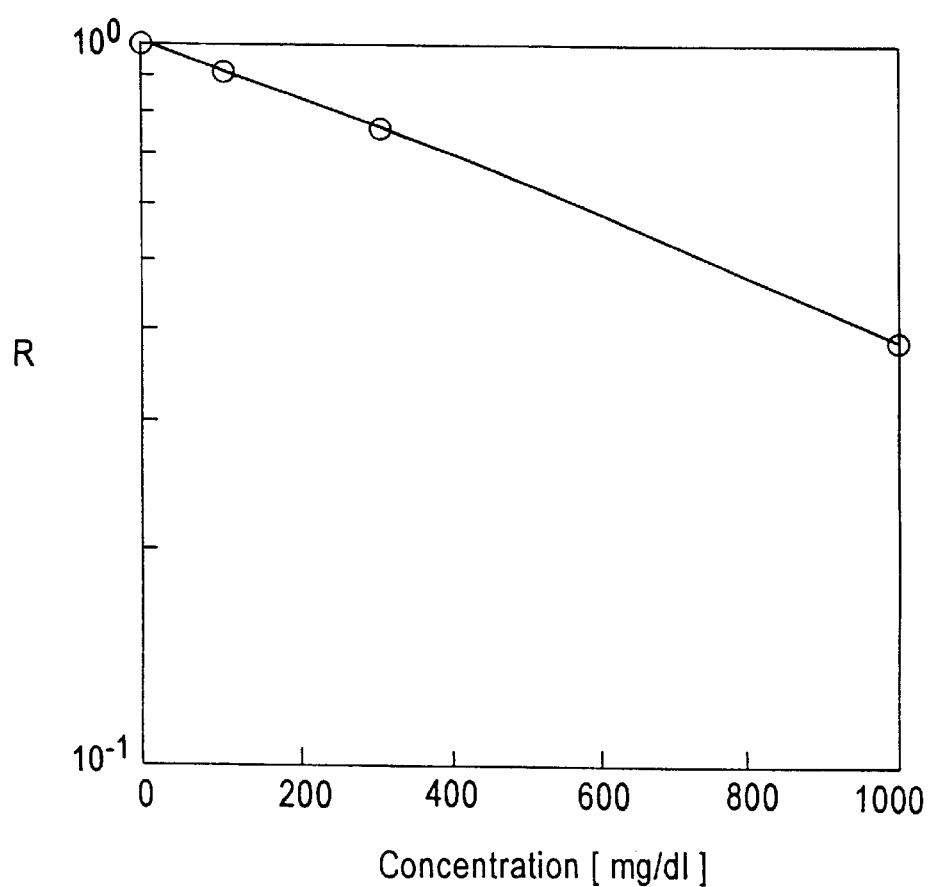
FIG. 5 is a characteristic diagram illustrating the relation between the albumin concentration of the solution known from the preceding measurement and R (ratio of the intensity of the transmitted light at 70° C. to that at 75° C.).

The procedure of urinalysis in the present embodiment is hereinafter described. Albumin solutions with a concentration of 100, 300 or 1,000 mg/dl were prepared using urine as a solvent of which an albumin concentration had been found to be not higher than 10 mg/dl by using a test paper. These albumin solutions and the urine used as the solvent were poured into the respective sample cells 12 and heated from 35° C. to 80° C. at a rate of 2° C./min. While heating the samples, the intensity of the transmitted light was determined every 6 seconds. The results are plotted in FIG. 4, with the axis of abscissas representing the temperature of the sample and the axis of ordinates the lock-in amplifier output voltage for each concentration of sample which corresponds to the intensity of the transmitted light. Also plotted in FIG. 5 is the ratio R which indicates a ratio of the intensity of light transmitted through the liquid sample at 75° C. to that at 70° C. as defined below.

R=(intensity of transmitted light at 75° C.)/(intensity of transmitted light at 70° C.)

R is indicated logarithmically on the axis of ordinates. As is apparent from FIG. 5, a relation between R and the albumin concentration of the liquid sample is approximated to a straight line. By using this straight line as an analytical line, therefore, determination can be made of the concentration of albumin or protein level in an unknown urine sample. The method of the present embodiment allows more accurate determination than that in Example 1, because it is possible to except impedimental factors such as a transmittance of the liquid sample before heating.

Using this apparatus, urine was tested that had been found to not lower than 100 mg/dl and not higher than 250 mg/dl in albumin concentration by using a test paper. R was 0.89. The albumin concentration of the urine was found to be 120 mg/dl from the R and the analytical line in FIG. 5. This value agrees with the results obtained by using the test paper.

Similarly, determination was also made of another urine which had been found to be not lower than 300 mg/dl and not higher than 500 mg/dl in albumin concentration by using a test paper. The result was that R was 0.67. From the R and the analytical line in FIG. 5, the albumin concentration of the urine was found to be 400 mg/dl, agreeing with the results obtained by using the test paper.

As shown, the method in the present embodiment allows accurate determination of protein concentration of the urine. Besides, no expendable supplies such as a test paper are required.

EXAMPLE 3

Figure 6:
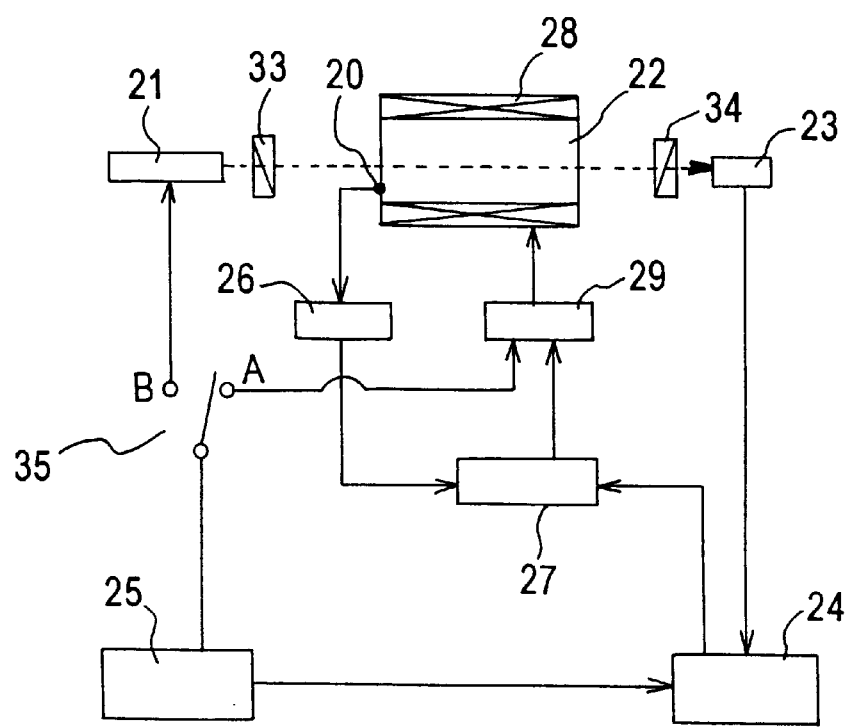
FIG. 6 is a schematic diagram showing the configuration of a measurement apparatus in a still further embodiment of the present invention.

The configuration of a measurement apparatus used in the present embodiment is shown in FIG. 6. In the present embodiment, an angle of rotation of a liquid sample was determined first at normal temperature. The sample was then heated. While heating, measurement was taken of the temperature of the sample and the intensity of a light transmitted through the sample.

The basic principle of measuring the angle of rotation by the present apparatus is the optical zero-order method based on the vibration of the plane of polarization using the Faraday effect. An irradiation module 21 is the same as the one used in Example 1 and projects substantially parallel light rays with a wavelength of 670 nm and an intensity of 5 mW. An polarizer 33 transmits only the component of a specific direction out of the projected light rays. A sample cell 22 is the same as the one used in Example 1. The liquid sample placed in it modulates the direction of polarization of the transmitting light rays by a very small width due to the optical Faraday effect. An analyzer 34 is arranged in the orthogonal Nicol state in relation to a polarizer 33 at first, and rotates with the transmission axis of the polarizer 33 as an axis of rotation. If the polarizer 33 and the analyzer 34 are ideal ones, that is, the extinction ratio is infinite, then the transmitted light does not reach a photosensor 23. In practice, however, the extinction ratio of a polarizer and an analyzer can not be infinite. The extinction ratio of the polarizer 33 and the analyzer 34 used in the present embodiment is approximately 5,000, and therefore some 1 $\mu$W of the transmitted light arrives at the photosensor 23. This intensity of light is enough for determination of the intensity of the transmitted light.

A lock-in amplifier 24 makes phase-sensitive detection of an output signal of a photosensor 23, referring to a modulated signal emitted to the irradiation module 21 from a signal generator 25.

When the angle of rotation is determined, a switch 35 is connected to the terminal A to supply to a coil-shaped heater driver 29 the signal of the signal generator 25 as a magnetic field modulation signal. When measuring the transmitted light, the switch 35 is connected to the terminal B to send the signal to the irradiation module 21 as a modulation signal of the projected light.

The heater driver 29 supplies a heater 28 with a current of up to 5 A in accordance with a command from a computer 27. In determining the angle of rotation, however, the heater 28 and heater driver 29 apply a magnetic field on the liquid sample in the sample cell 22 in accordance with a command from the computer 27. They can also sweep this magnetic field while modulating it. In other words, the heater 28 in the present apparatus can apply a magnetic field on the liquid sample when determining the angle of rotation and performs its original function as a heater when the liquid sample is heated. A thermocouple 20, mounted close to the sample cell 22, practically detects the temperature of the sample in the sample cell 22. A temperature indicator 26 indicates a temperature of the sample detected by the thermocouple 20 and sends the value to the computer 27 at the same time.

In that setup, the angle of rotation is first determined in accordance with the command from the computer 27, and then determination is made of the temperature of the sample and the intensity of the light transmitted through the sample while heating the sample. By this, it is possible to determine the sugar and protein levels in the sample by one measurement.

The procedure of testing urine using the present apparatus is hereinafter explained.

First, albumin solutions with a concentration of 100, 300 and 1,000 mg/dl were-prepared with urine as a solvent of which the albumin concentration had been found to be not higher than 10 mg/dl by using a test paper. These albumin solutions and the urine used as the solvent were placed in the respective sample cells 22 and heated from 35° C. to 80° C. With a heating velocity set at 2° C., the intensity of the transmitted light was determined every 6 seconds.

The ratio R that is a ratio of the intensity of the light transmitted through the solution at 75° C. to that at 70° C. was calculated in the same way as in Example 2. The ratio R was plotted in relation to the respective concentrations in FIG. 7, with the axis representing R logarithmically.

Figure 7:
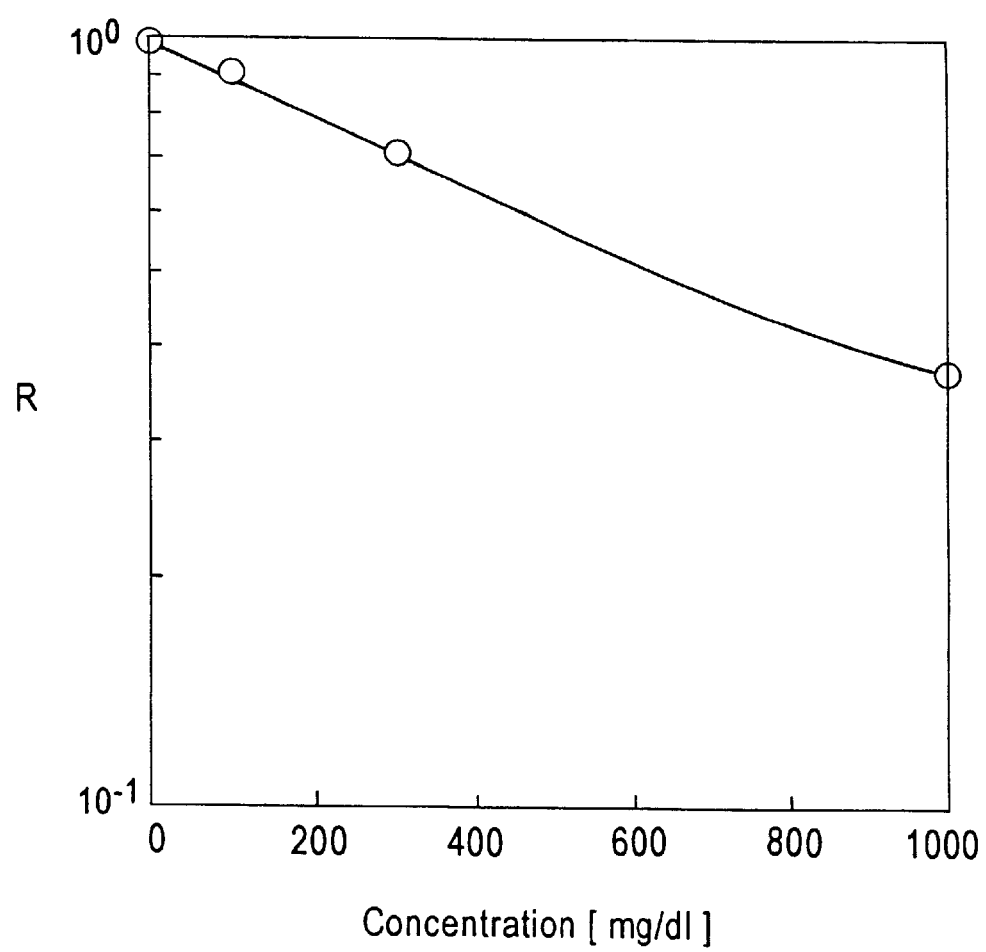
FIG. 7 is a characteristic diagram showing the relation between the albumin concentration in the aqueous solution known from a measurement using the same apparatus and R (ratio of the intensity of the transmitted light at 70° C. to that at 75° C.).

With the curve in FIG. 7 as an analytical line, the albumin concentration in the urine or the urine protein level can be determined. It is noted that the degree of polarization of a linearly polarized light propagating through the urine decreases with the rise of turbidity. That is, polarization is canceled by scattering. Because of this cancellation of polarization, therefore, the analytical line in FIG. 7 is not a straight line unlike that obtained in Example 2 and shown in FIG. 5.

Using the present apparatus, determination was then made the same way as above of a urine sample of which the glucose concentration had been found to be not higher than 50 mg/dl, and the albumin concentration not lower than 100 mg/dl and not larger than 250 mg/dl by using test papers.

First, the angle of rotation was determined. The result was:

$$A = -19.8 \times 10^{-3} \text{ [degrees]}$$

Then, the urine sample was heated and determination was made of the intensity of the transmitted light. From this was obtained:

$$R = 0.85$$

From this ratio R and the analytical line in FIG. 7, the albumin concentration was determined to be 120 mg/dl. By solving equation (2) with that albumin concentration and A, the glucose concentration was found to be 30 mg/dl. These are in agreement with the results obtained by using the test papers.

Using the present apparatus, another urine sample was also tested of which the glucose concentration had been found to be not lower than 100 mg/dl and not higher than 250 mg/dl, and the albumin concentration not lower than 300 mg/dl and not larger than 500 mg/dl by using test papers.

First, the angle of rotation was determined. The result was:

$$A = -56 \times 10^{-3} \text{ [degrees]}$$

Then, the urine sample was heated and determination was made of the intensity of the transmitted light. From the result was obtained:

$$R = 0.62$$

From this ratio R and the analytical line in FIG. 7, the albumin concentration was determined to be 400 mg/dl. By solving equation (2) with the albumin concentration and A, the glucose concentration was found to be 150 mg/dl. These are in agreement with the results obtained by using the test papers.

According to the present embodiment as shown, the urine protein level and urine sugar level can be determined by one measurement if the angle of rotation of the urine is first measured, and the sample is then opacified by heating and its white turbidity is measured. This way, the urine protein level and urine sugar level can be measured without using expendable supplies such as a test paper. Thus this method is high in practicality.

EXAMPLE 4

Figure 8:
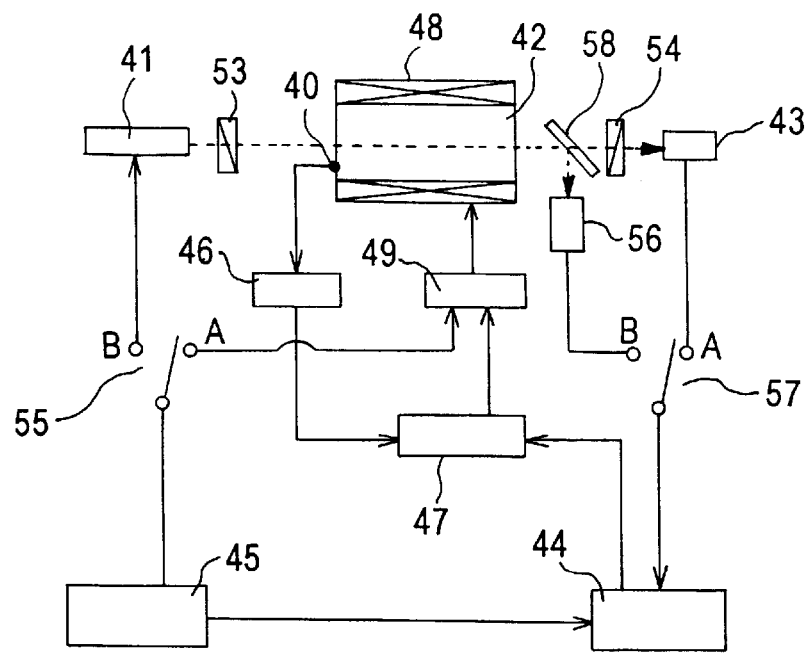
FIG. 8 is a schematic diagram showing the configuration of a measurement apparatus in still another embodiment of the present invention.

The method in the present embodiment is hereinafter explained in detail with reference to FIG. 8.

In the present embodiment, too, an angle of rotation of urine is first measured. Then the intensity of light transmitted through the urine is measured while heating the urine and measuring the temperature of the urine.

The basic principle of measuring the angle of rotation of the present apparatus is the same as that in Example 3.

As in Example 1, a polarizer 53 transmits only the component of a specific direction out of substantially parallel light rays projected by an irradiation module 41. A sample cell 42 is the same as the one used in Example 1. A liquid sample placed in it modulates the direction of polarization of the transmitting light by a very small width due to the optical Faraday effect. A polarizer 53 and an analyzer 54 are arranged in the orthogonal Nicol state. When the angle of rotation is determined, a switch 55 is connected to the terminal A to supply to a coil-shaped heater driver 49 a signal of a signal generator 45 as a magnetic field modulation signal. When measuring the transmitted light, the switch 55 is connected to the terminal B to send a signal to the irradiation module 41 as a modulation signal of the light to be projected. A beam sampler 58 takes out part of the light transmitted through the liquid sample. A photosensor 56 detects the light taken out and emits a signal according to the intensity of the light. The switch 57, synchronized with the switch 55, is so changed over that an output signal of a photosensor 43 is supplied to a lock-in amplifier 44 when measuring the angle of rotation and the output signal of the photosensor 56 is supplied to a lock-in amplifier 44 when measuring the transmitted light. In measuring the angle of rotation, a heater 48 and the heater driver 49, as in Example 3, apply a magnetic field on the liquid sample in accordance with a command from a computer 47. They can also sweep the magnetic field while modulating it. A thermocouple 40, mounted close to the sample cell 42, practically detects the temperature of the liquid sample in the sample cell 42. A temperature indicator 46 indicates the temperature of the liquid sample detected by the thermocouple 40 and sends the value to the computer 47 at the same time.

In the present embodiment as in Example 3, the angle of rotation of the liquid sample is first measured, and the intensity of the transmitted light are determined, while heating the sample and measuring the temperature of the sample. But the present embodiment is not subject to effects of the cancellation of polarization unlike Example 3. So, a straight analytical line can be obtained. Actually, the straight analytical line was obtained in an analysis with the same albumin solution as in Example 3.

Using the present apparatus, a measurement was conducted on a urine sample of which the glucose concentration had been found to be not higher than 50 mg/dl, and the albumin concentration not lower than 100 mg/dl and not larger than 250 mg/dl by using test papers. First, the angle of rotation was determined. The result was:

$$A = -19.8 \times 10^{-3} \text{ [degrees]}$$

Then, the urine sample was heated and determination was made of the intensity of the transmitted light. From the result was obtained:

$$R = 0.89$$

From this ratio R and the analytical line obtained, the albumin concentration was determined to be 120 mg/dl. By solving equation (2) with that albumin concentration and A, the glucose concentration was found to be 30 mg/dl. These are in agreement with the results obtained by using the test papers.

Similar measurement was conducted on another urine sample of which the glucose concentration had been found to be not lower than 100 mg/dl and not higher than 250 mg/dl, and the albumin concentration not lower than 300 mg/dl and not larger than 500 mg/dl by using test papers. First, the angle of rotation was determined. The result was:

$$A = 56 \times 10^{-3} \text{ [degrees]}$$

Then, the urine sample was heated and determination was made of the intensity of the transmitted light. From the result was obtained:

$$R = 0.67$$

From this ratio R and the analytical line obtained, the albumin concentration was determined to be 400 mg/dl. By solving equation (2) with the albumin concentration and A, the glucose concentration was found to be 150 mg/dl.

These are in agreement with the results obtained by using the test papers.

According to the present embodiment as shown, the urine protein level and urine sugar level can be determined by one measurement if the angle of rotation of the urine sample is measured in advance to heat the urine sample and measure the intensity of the light transmitted through the sample whereby determining its white turbidity. In this way, the urine protein level and urine sugar level can be measured without using expendable supplies like a test paper. Thus this method is high in practicality. Especially in the present embodiment, the conversion from R to the albumin concentration is easy since a straight analytical line can be obtained.

In those embodiments, the methods have been explained of finding the urine protein level on the base of the intensity of the light transmitted through the urine. In the following embodiments, an explanation is made about procedures for determining the urine protein level from the intensity of a light scattered from the urine.

EXAMPLE 5

Figure 9:
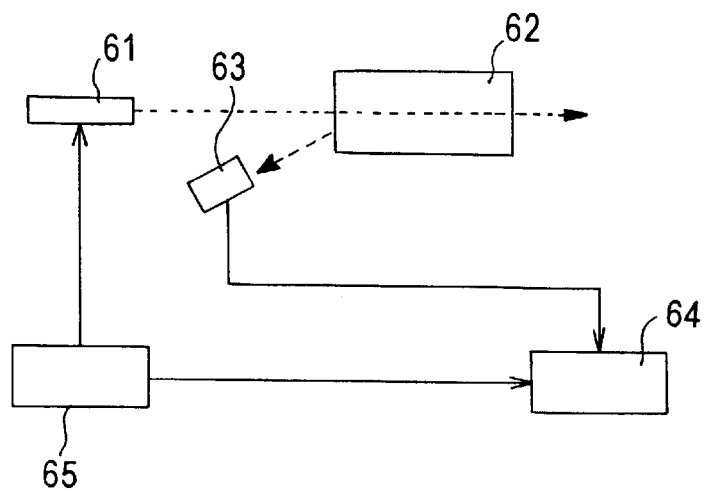
FIG. 9 is a schematic diagram showing the configuration of a measurement apparatus in yet another embodiment of the present invention.

A method based on a measurement of an intensity of a light scattered from a sample is hereinafter explained in detail with reference to FIG. 9. As in Example 1, an irradiation module 61 projects light rays to a sample cell 62. A liquid sample is placed in the sample cell 62. The light rays projected from an irradiation module 61 and scattered when passing through the sample in the sample cell 62 is detected by a photosensor 63, which then outputs a signal. A lock-in amplifier 64 makes phase-sensitive detection of an output voltage of the photosensor 63 referring to a modulation signal emitted to an irradiation module 61 from a signal generator 65 and then outputs a signal corresponding to the intensity of the scattered light. The signal generator 65 supplies a modulation signal to the irradiation module 61 so as to pulse-insulate the light to be projected from the irradiation module 61 in synchronization with this signal.

Using this apparatus, a measurement was taken of the intensity of the light scattered on a urine sample which had been heated and then cooled. Albumin solutions with a concentration of 100, 300 or 1,000 mg/dl were prepared with urine as a solvent of which the albumin concentration had been found to be not higher than 10 mg/dl by using a test paper. These albumin solutions were heated along with the urine used as the solvent for 5 minutes at 75° C. and cooled down to 35° C. They were then poured into-the respective sample cells 62, and the intensity of the scattered light was determined.

Figure 10:
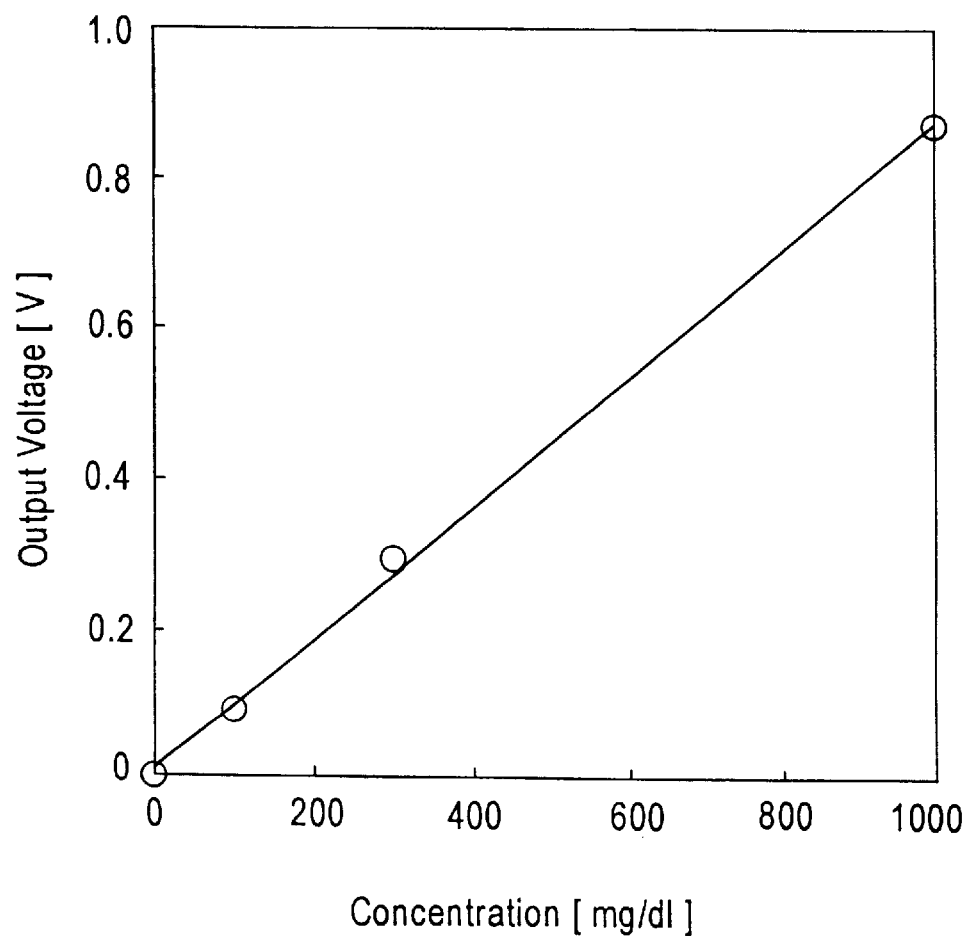
FIG. 10 is a characteristic diagram showing the output voltage in relation to the albumin concentration of the aqueous solution in the same measurement apparatus.

The results or the output voltage from the lock-in amplifier 64 are plotted in FIG. 10. There, the output voltage is indicated logarithmically on the axis of ordinates and the concentration of albumin solution on the axis of abscissas. The concentration of 0 represents the solvent alone or the urine. As indicated, a relation between the output voltage and the albumin concentration is linearly approximated to a straight line in the determination of the scattered light, too. By using this straight line as an analytical line, therefore, it is possible to determine the concentration of albumin or protein level in the sample.

Using this apparatus, a urine sample was tested that had been found to not lower than 100 mg/dl and not higher than 250 mg/dl in albumin concentration by using a test paper. It showed that the output voltage of the lock-in amplifier 64 was 0.12 V. The concentration of albumin as found from the analytical line shown in FIG. 10 was 120 mg/dl, agreeing with the results obtained by using the test paper.

The same way, another urine sample was tested that had been found to not lower than 300 mg/dl and not higher than 500 mg/dl in albumin concentration by using a test paper. The result was that the output signal intensity of the lock-in amplifier 64 was 0.35 V. The concentration of albumin as found from the analytical line shown in FIG. 10 was 400 mg/dl. It is in agreement with the results obtained by using the test paper.

As shown, the urine protein level and urine sugar level can be measured according to the method of the present embodiment. This method also requires no expendable supplies like test paper, in addition.

EXAMPLE 6

Figure 11:
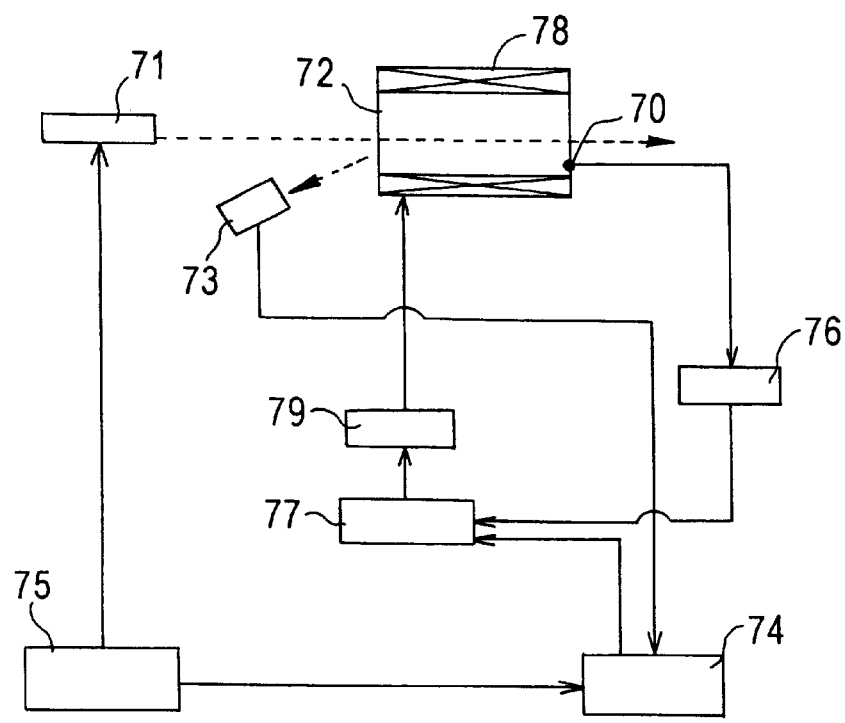
FIG. 11 is a schematic diagram showing the configuration of an apparatus in a still further embodiment of the present invention.

The configuration of an apparatus used in the present embodiment is shown in FIG. 11. In the present embodiment, while heating a liquid sample and measuring the temperature thereof, the intensity of the light scattered from the liquid sample is determined. As in Example 1, an irradiation module 71 projects light rays to a sample cell 72. A liquid sample heat-treated at a specific temperature is placed in the sample cell 72. A photosensor 73 detects the light scattered from the liquid sample on propagating through the sample cell 72 after being projected from the irradiation module 71. A lock-in amplifier 74 makes phase-sensitive detection of the output signal of the photosensor 73 referring to a modulated signal emitted to the irradiation module 71 from a signal generator 75 and then outputs a signal corresponding to the intensity of the scattered light. There, the signal generator 75 supplies a modulation signal to the irradiation module 71 so as to pulse-modulate the light rays from the irradiation module 71 in synchronization with this signal. Around the sample cell 72 is arranged the same heater 78 as that in Example 3. A coiled heater driver 79 supplies the heater 78 with current of up to 5 A according to the command from the computer 77. A thermocouple 70, mounted close to the sample cell 72, practically detects the temperature of the liquid sample in the sample cell 72. A temperature indicator 76 indicates the temperature of the liquid sample detected by the thermocouple 70 and sends the value to the computer 77 at the same time. The output of a lock-in amplifier 74 or the intensity of the scattered light is also sent to the computer 77. The computer 77 then heats the liquid sample according to the preset program and measures the temperature of the liquid sample and the intensity of the scattered light.

Figure 12:
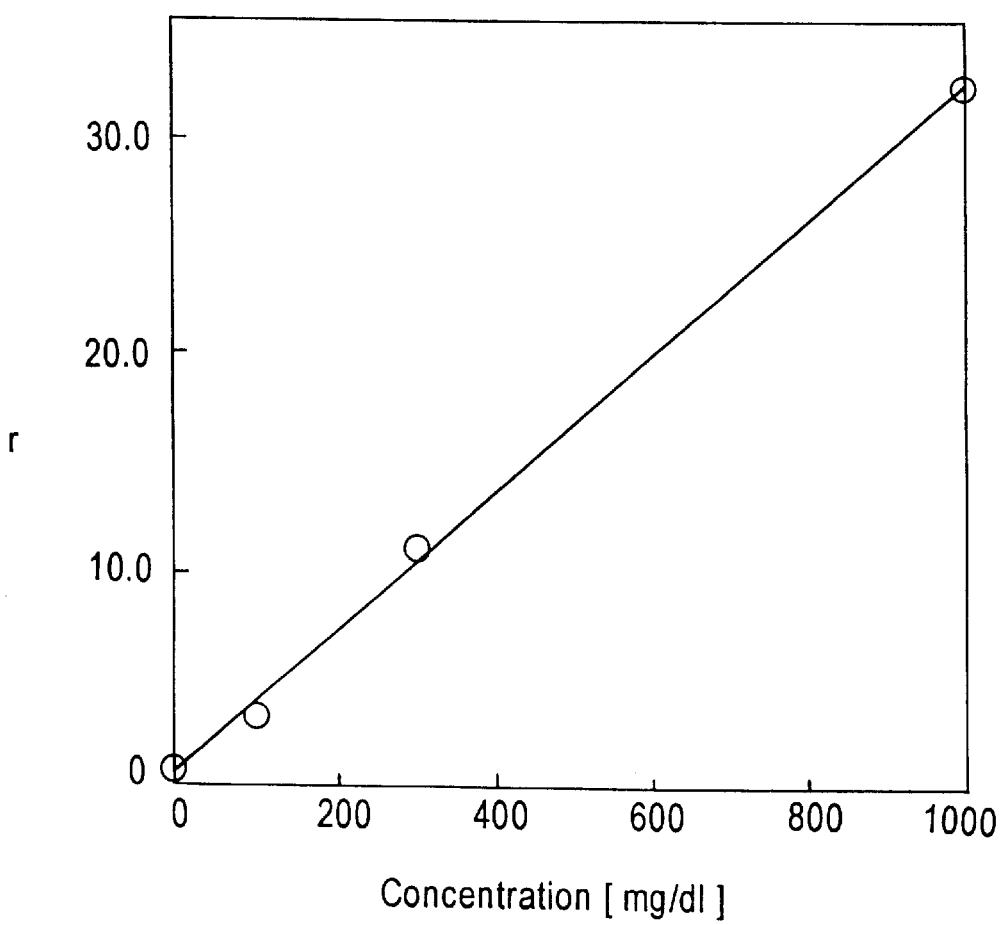
FIG. 12 is a characteristic diagram showing the relation between the albumin concentration of the aqueous solution known from the same measurement and r (ratio of the intensity of the scattered light at 70° C. to that at 75° C.).

The urinalysis method of the present embodiment is hereinafter described. Albumin solutions with a concentration of 100, 300 or 1,000 mg/dl were prepared with urine as a solvent of which the albumin concentration had been found to be not higher than 10 mg/dl by using a test paper. These albumin solutions and the urine used as the solvent were placed in the respective sample cells 72 and heated from 35° C. to 80° C. at a rate of 2° C./minute. While heating, the intensity of the scattered light was measured every 6 seconds. Plotted in FIG. 12 is the ratio r that is a ratio of the intensity of light scattered at 75° C. to that at 70° C. with that albumin concentration. The ratio r is defined as follows:

r=(intensity of light scattered at 75° C.)/(intensity of light scattered at 70° C.)

where r is indicated logarithmically on the axis of ordinates. As is cleared from FIG. 12, a relation between the concentration of albumin and r is approximated by a straight line. By using this straight line as an analytical line, determination can be made of the albumin concentration or protein level in an unknown urine sample. The method of urinalysis in the present embodiment allows more accurate determination than that in Example 5, because it is possible to except impedimental factors such as the transmittance of the sample before heating.

Using this apparatus, a urine sample was tested that had been found to not lower than 100 mg/dl and not higher than 250 mg/dl in albumin concentration by using a test paper. The ratio r was found to be 4.6. With this, the albumin concentration was found to be 120 mg/dl from the analytical line in FIG. 12. It agrees with the results by using the test paper.

Similarly, another urine sample was tested of which the albumin concentration had been found to be not lower than 300 mg/dl and not higher than 500 mg/dl by using test papers. The ratio R was found to be 13.3. With this value, the concentration of albumin was found to be 400 mg/dl from the analytical line in FIG. 12. It is in agreement with the results obtained by using the test papers. As shown, the urine protein level can be measured with high accuracy by the present method. Besides, no expendable supplies like test paper are required.

EXAMPLE 7

Figure 13:
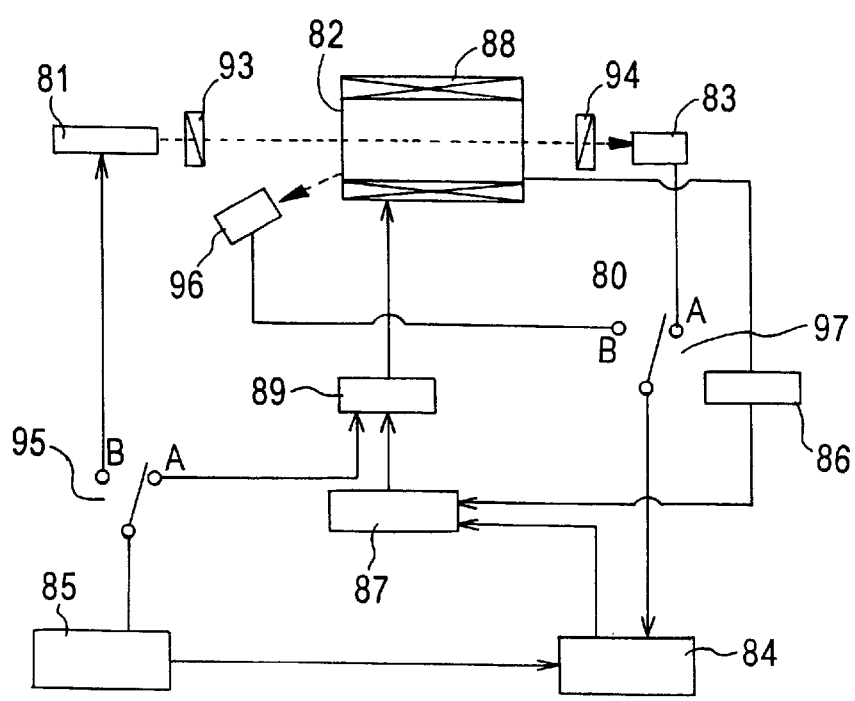
FIG. 13 is a schematic diagram showing the configuration of a measurement apparatus in a still another embodiment of the present invention.

A method in the present embodiment is hereinafter described in detail with reference to FIG. 13. In the present embodiment, the angle of rotation of a liquid sample is first measured. Then, while heating the liquid sample and measuring the temperature of the sample, an intensity of a light scattered from the sample is measured.

A polarizer 93 transmits only the component of a specific direction out of the substantially parallel light rays subjected by an irradiation module 81 as same as the one used in Example 1. A sample cell 82 is the same as the one used in Example 1. A liquid sample placed in it modulates the direction of polarization of the transmitted light by a very small width. A polarizer 93 and an analyzer 94 are positioned in the orthogonal Nicol state with the sample cell 82 between them. Around the sample cell 82 is arranged a coil-shaped heater 88. When the angle of rotation is measured, a switch 95 is connected to the terminal A to supply to a coil-shaped heater driver 89 a signal of a signal generator 85 as a magnetic field modulation signal. When measuring the scattered light, the switch 95 is connected to the terminal B to send the signal to the irradiation module 81 as an modulation signal of the projected light. A photosensor 96 detects the light scattered in passing through the liquid sample in the sample cell 82 after being projected from the irradiation module 81. A switch 97 is so changed over that the output signal of the photosensor 83 is supplied to a lock-in amplifier 84 when measuring the angle of rotation and the output signal of a photosensor 96 is supplied to the lock-in amplifier 84 when measuring the scattered light. A thermocouple 80, installed close to the sample cell 82, practically detects the temperature of the liquid sample in the sample cell 82. A temperature indicator 86 indicates the temperature of the liquid sample detected by the thermocouple 80 and sends the value to a computer 87 at the same time.

That way, as in Example 6, after measuring the angle of rotation of the liquid sample, the temperature of the sample and the intensity of the scattered light is determined while heating the sample.

A urine sample was tested of which the glucose concentration had been found to be not higher than 50 mg/dl, and the albumin concentration not lower than 100 mg/dl and not larger than 250 mg/dl by using test papers.

First, the angle of rotation was determined. The result was:

$$A=-19.8 \times 10^{-3} \text{ [degrees]}$$

Then, the urine sample was heated and determination was made of the intensity of the scattered light, and the following was obtained:

$$r=4.6$$

From this ratio r and the analytical line obtained, the albumin concentration was determined to be 120 mg/dl. By solving equation (2) with that albumin concentration and A, the glucose concentration was found to be 30 mg/dl. These are in agreement with the results obtained by using the test papers.

Similarly, urinalysis was made of another urine sample which the glucose concentration had been found to be not lower than 100 mg/dl and not higher than 250 mg/dl, and the albumin concentration not lower than 300 mg/dl and not larger than 500 mg/dl by test papers.

First, the angle of rotation was determined. The result was:

$$A=-56 \times 10^{-3} \text{ [degrees]}$$

Then, the urine sample was heated and determination was made of the intensity of the scattered light, and the following was obtained:

$$r=13.7$$

From this ratio r and the analytical line obtained, the albumin concentration was determined to be 400 mg/dl. By solving equation (2) with the albumin concentration and A, the glucose concentration was found to be 150 mg/dl. These are in agreement with the results obtained by using the test papers.

As shown, the method in the present embodiment allows determinations of urine protein and sugar levels together if the angle of rotation is first measured in advance to opacify the urine sample by heating and to measure the white turbidity of the urine sample. In this way, it is possible to find the urine protein level and sugar level without using expendable supplies like a test paper.

Noteworthy is that in the present embodiment, only one photosensor is required as in the apparatus in the above embodiment.

As shown above in the embodiments, the urine protein level of the sample can be measured by heating the sample so as to opacify it and determining the white turbidity of the sample from the intensity of the transmitted or scattered light. Also, if the angle of rotation of the sample is measured before heating, the urine protein level and sugar level as well can be obtained.

According to the present invention, a urinalysis method can be realized which requires no expendable supplies like test paper, thus providing a urinalysis apparatus easy to maintain and operate.

EXAMPLE 8

According to the preceding embodiments, urine protein and sugar levels can be determined accurately in most urine samples. However, there are some samples which are difficult to opacify by heating. Urine samples with an abnormally high pH value, for example, will not turn white, because the albumin does not coagulate well. A urine sample of Comparative Example illustrated in FIG. 14 had been found to be in a range of 300–500 mg/dl in protein level by using a test paper and had a pH value of 7.0. An intensity of a transmitted light though the urine sample of Comparative Example was observed as same in Example 1 after heating the urine sample for 5 minutes at 80° C. and cooling down it to 35° C. As indicated, white turbidity of the urine sample by heating is low and is far apart from the analytical line in Example 1 which is represented by a broken line.

With such urine samples, the addition of bivalent metal irons, i.e. calcium irons and magnesium ions can facilitate the coagulation of albumin in the urine sample.

Albumin aqueous solutions were prepared which were 100, 300 and 1,000 mg/dl in concentration. Then, those aqueous solutions and pure water as a reference, 1 dl each, were mixed with 22.2 mg of calcium chloride. The aqueous solutions thus prepared were each heated for 5 minutes at 80° C. and then cooled to 35° C. The heat-treated samples were separately poured into a sample cell 2 and the transmitted light was observed.

On the other hand, 22.2 mg of calcium chloride was dissolved in the same urine sample as in Comparative Example. The Urine sample was heated and the transmitted light was observed. This shall be Example 8.

Figure 14:
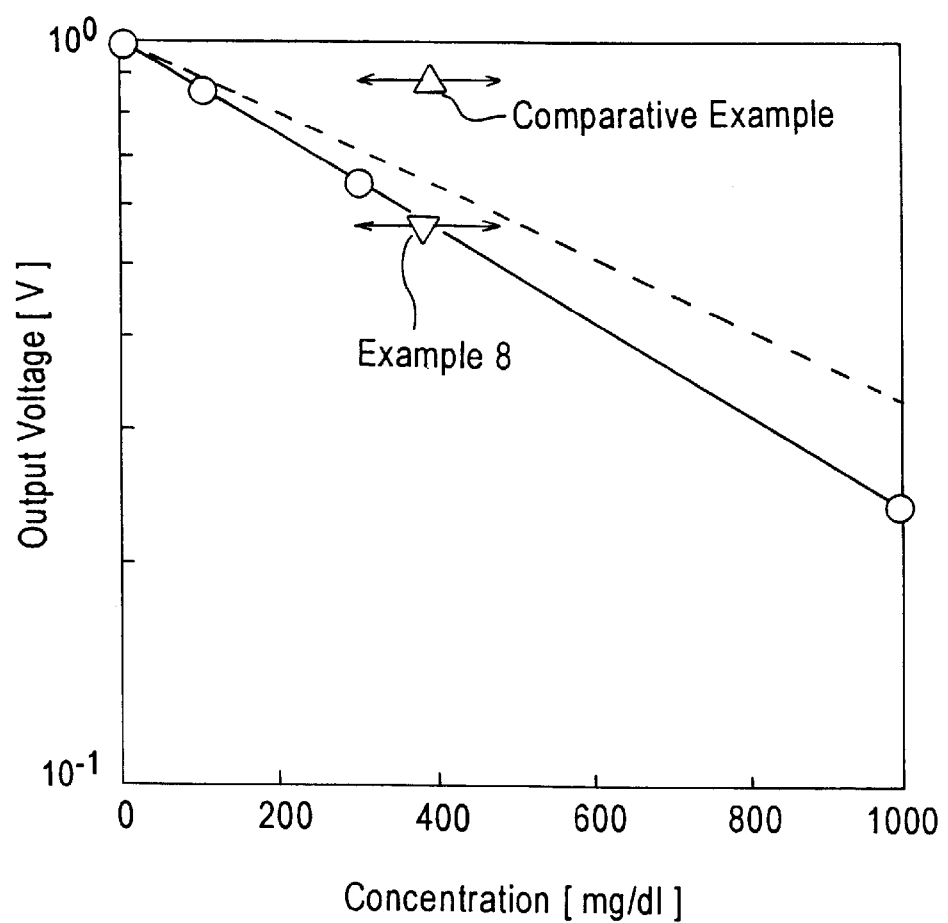
FIG. 14 is a characteristic diagram showing the relation between the concentration of albumin in urine mixed with potassium chloride and the output voltage of the photosensor known from yet another embodiment of the present invention.

Those results are shown in FIG. 14. As is evident from the figure, the addition of calcium chloride can facilitate the coagulation of albumin in the urine, permitting an accurate determination of the urine protein level.

Then, the effect of the addition of calcium chloride to the urine was visually observed. It showed that the white turbidity of the urine rose with the increase in an additive amount of calcium chloride. But when the amount of calcium chloride exceeded 0.2 m mol (millimole)/dl of the urine, the white turbidity did not change any more. From this, it follows that albumin in the urine can be completely coagulated by adding 0.2 m mol or more/dl urine.

But the analytical line also changes with the addition of those bivalent metal ions unlike when no addition is made. Therefore, it is necessary to prepare the analytical line of the aqueous albumin solution mixed with the same amount of calcium chloride as that added to the test urine sample.

Figure 15:
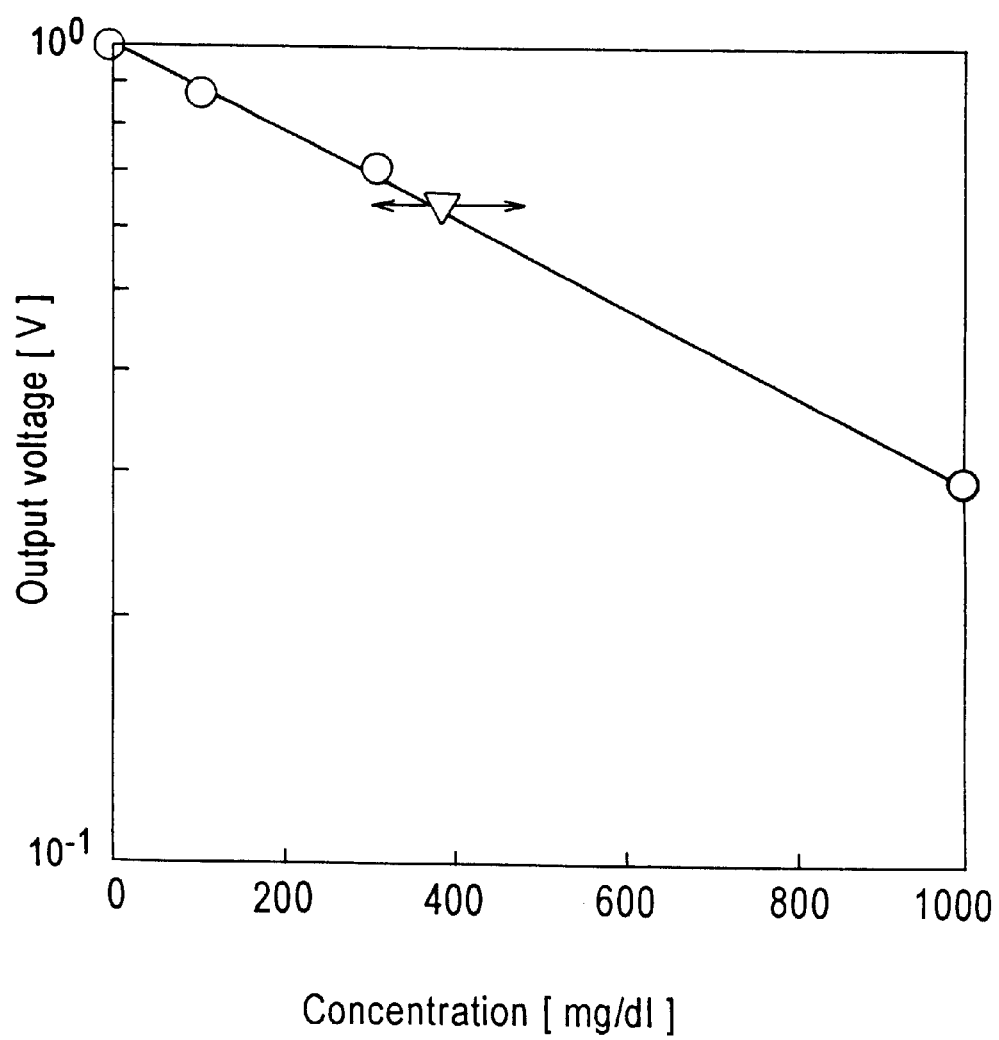
FIG. 15 is a characteristic diagram showing the relation between the concentration of albumin in urine mixed with magnesium chloride and the output voltage of the photosensor known from the same embodiment of the present invention.

A study was made of the addition of magnesium chloride to the same urine sample as above. It was confirmed that the addition of magnesium chloride in place of calcium chloride facilitates the coagulation of albumin in the urine the same way. In this test, when the additive amount of magnesium chloride exceeded 0.1 m mol/dl urine, the white turbidity became unchanged. Magnesium chloride was added to urine in 9.5 mg/dl. With this solution, the transmitted light was observed the same way as above. The results are shown in FIG. 15. From this, it was confirmed that accurate measurements were possible with magnesium chloride, too.

EXAMPLE 9

In the present embodiment, an acid was added to a urine sample which was difficult to opacify by heating. It is possible to facilitate the coagulation of albumin by lowering the pH value of the urine sample with an acid like acetic acid.

A 1% aqueous solution of acetic acid was added to the same urine sample as in Embodiment 8 in 0.1 ml/dl, thereby opacifying the urine sample. Upon addition of the acidic solution, the pH value of the urine sample decreased to 5.5. The sample was heated for 5 minutes at 80° C. and cooled down to 35° C. The heat-treated urine sample was placed in the sample cell 1, and measurements were taken of the intensity of the transmitted light. The measurement was also taken to the urine alone, as a reference.

On the other hand, albumin aqueous solutions were prepared which had a concentration of 100, 300 or 1,000 mg/dl. Those aqueous solutions and pure water as a reference were mixed with 0.1 ml of the acid/dl, respectively. Thus obtained were each heated for 5 minutes at 80° C. and cooled down to 35° C. Then the similar measurements were taken of the intensity of the transmitted light.

The results are shown in FIG. 16. As shown, the urine protein level can be determined with high accuracy when the acid is added in place of bivalent metal ions in Example 8. It was also confirmed that even if the pH value of the urine sample is further lowered by increasing the amount of additive acetic acid, the urine protein can be determined accurately the same way.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A method of measuring a concentration of specific constituent in a liquid sample which comprises the steps of:

heating a liquid sample containing protein to obtain an opacified liquid sample;

projecting a light on said opacified liquid sample;

detecting the component transmitted through said opacified liquid sample or scattered from said opacified liquid sample out of the projected light; and determining a concentration of protein in said opacified liquid sample on the basis of intensity of the detected light.

2. The method of measuring a concentration of a specific constituent in a liquid sample in accordance with claim 1, wherein said liquid sample is urine.

3. The method of measuring a concentration of a specific constituent in accordance with claim 2, wherein said light has a wavelength of not shorter than 500 nm.

4. The method of measuring a concentration of a specific constituent in accordance with claim 2, further comprising the steps of:
   measuring an angle of rotation of said liquid sample before heating; and
   determining the urine sugar level in said liquid sample on the basis of said angle of rotation of said liquid sample and urine protein level obtained.

5. The method of measuring a concentration of a specific constituent in accordance with claim 1, wherein the step of projecting said light is performed in the step of heating said liquid sample.

6. The method of measuring a concentration of a specific constituent in accordance with claim 5, wherein said light is projected to said liquid sample at two temperatures in a range of 60° C. to 80° C., and the protein concentration in said liquid sample is determined on the basis of the ratio of the intensities of transmitted or scattered light obtained.

7. The method of measuring a concentration of a specific constituent in accordance with claim 1, further comprising the step of adding bivalent metal irons to the liquid sample before heating.

8. The method of measuring a concentration of a specific constituent in accordance with claim 7, wherein said bivalent metal ions are calcium ions or magnesium ions.

9. The method of measuring a concentration of a specific constituent in accordance with claim 8, wherein said calcium ions are added to said liquid sample in a ratio of 0.2 millimole or more per dl of said liquid sample.

10. The method of measuring a concentration of a specific constituent in accordance with claim 8, wherein said magnesium ions are added to said liquid sample in a ratio of 0.1 millimole or more per dl of said liquid sample.

11. The method of measuring a concentration of a specific constituent in accordance with claim 8, wherein said calcium ions or magnesium ions are added as chloride to said liquid sample.

12. The method of measuring a concentration of a specific constituent in accordance with claim 1, wherein an acid is added to said liquid sample before heating, thereby lowering the pH value of said liquid sample to 5.5 or below.

13. The method of measuring a concentration of a specific constituent in accordance with claim 12, wherein said acid is acetic acid or phosphoric acid.

* * * * *